(12) United States Patent
Lord et al.

(10) Patent No.: US 6,396,056 B1
(45) Date of Patent: May 28, 2002

(54) GAS DETECTORS AND GAS ANALYZERS UTILIZING SPECTRAL ABSORPTION

(75) Inventors: Harry C. Lord, Pasadena; Marc M. Baum, Baldwin Park, both of CA (US)

(73) Assignee: Air Instruments and Measurements, Inc., Baldwin Park, CA (US)

(*) Notice: Subject to any disclaimer, the term of this patent is extended or adjusted under 35 U.S.C. 154(b) by 0 days.

(21) Appl. No.: 09/348,204

(22) Filed: Jul. 8, 1999

(51) Int. Cl.$^7$ .................. G01N 21/35; G01N 21/61
(52) U.S. Cl. .............. 250/252.1; 250/339.09; 250/338.5
(58) Field of Search .............. 250/252.1, 338.1, 250/339.01, 339.09, 339.12, 341.5, 343, 341.8, 351, 354.1, 338.5

(56) References Cited

U.S. PATENT DOCUMENTS

| | | | | |
|---|---|---|---|---|
| 3,822,097 A | * | 7/1974 | Allington | 356/206 |
| 4,480,191 A | * | 10/1984 | Karpowycz | 250/343 |
| 4,549,080 A | * | 10/1985 | Baskins et al. | 250/343 |
| 4,746,218 A | * | 5/1988 | Lord, III | 356/437 |
| 5,184,017 A | * | 2/1993 | Tury et al. | 250/343 |
| 5,585,635 A | * | 12/1996 | Grahm | 250/343 |

* cited by examiner

Primary Examiner—Constantine Hannaher
Assistant Examiner—Albert Gagliardi
(74) Attorney, Agent, or Firm—David O'Reilly

(57) ABSTRACT

Instrumentation to detect the presence of, or to measure the concentration of, a gas or pollutant in a gaseous environment. With the use of spectroscopic techniques and energy beams having suitable wavelengths, the presence and concentrations of these can be detected and measured, not only in flowing streams such as in process streams or exhaust stacks, but above a ground area, around its perimeter, or across the road. A calibration means including an internal audit cell and a retrodirective reflector is also shown.

9 Claims, 7 Drawing Sheets

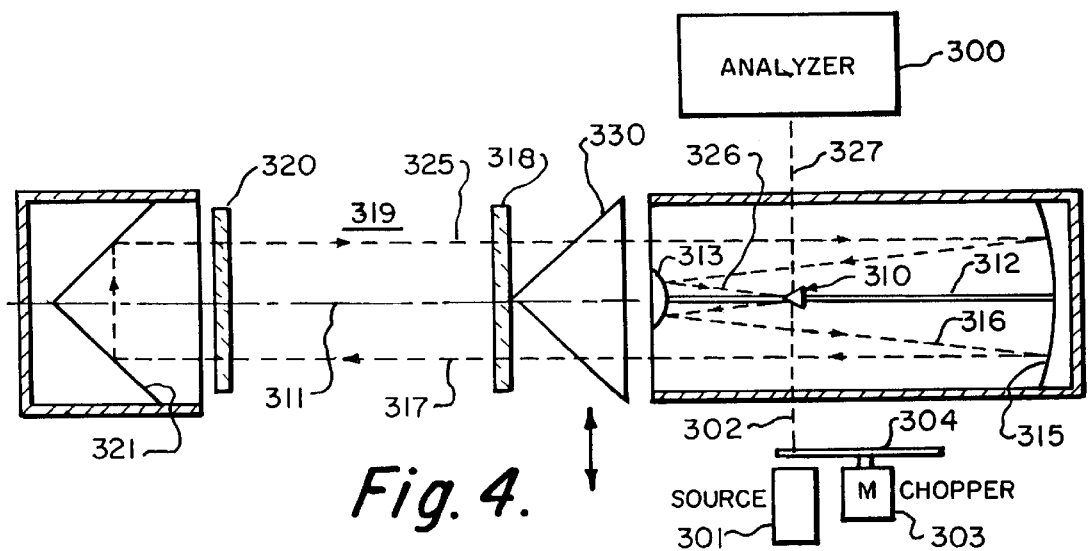
Fig. 4.
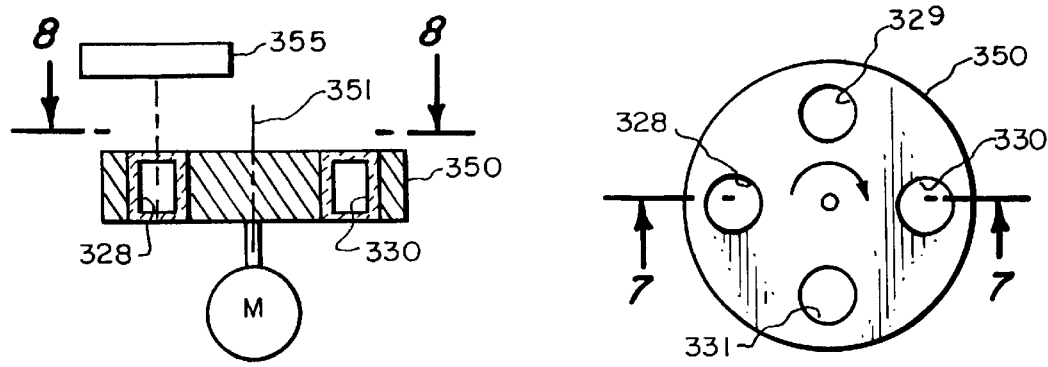
Fig. 7.
Fig. 8.
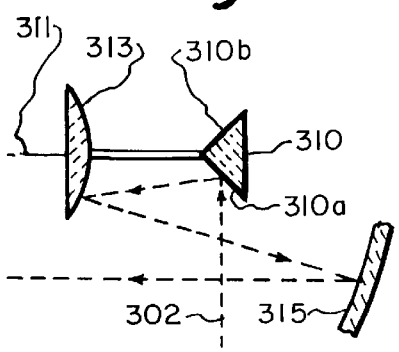
Fig. 9.
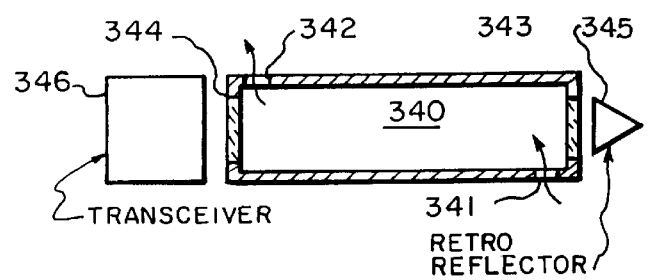
Fig. 10.

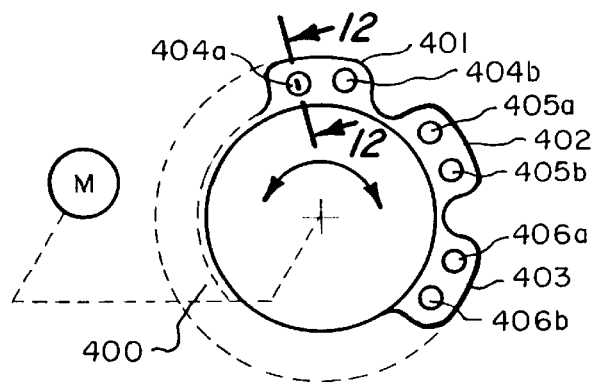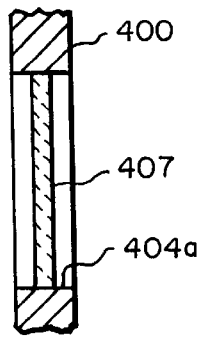
Fig. 11.    Fig. 12.
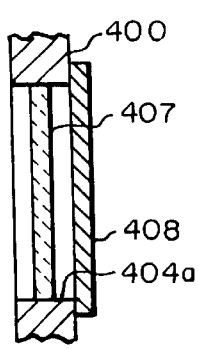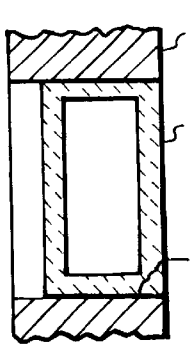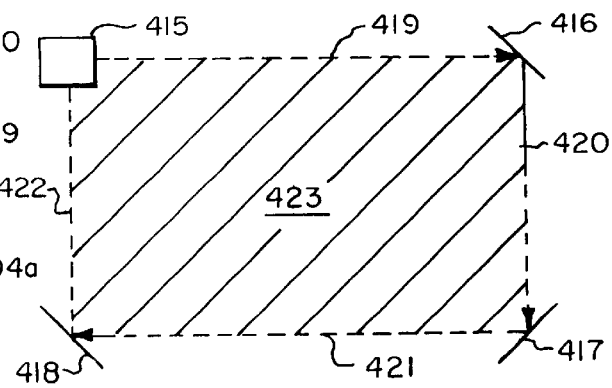
Fig. 13.    Fig. 14.    Fig. 15.
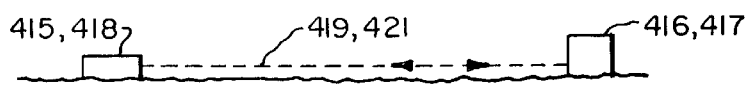
Fig. 16.
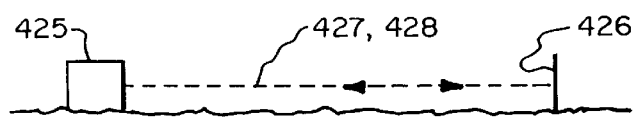
Fig. 17.

GAS DETECTORS AND GAS ANALYZERS UTILIZING SPECTRAL ABSORPTION

BACKGROUND OF THE INVENTION

1. Field of the Invention

This invention relates to instrumentation to detect the presence of, or to measure the concentration of, a gas or pollutant in a gaseous environment.

2. Background of the Invention

The detection of the presence of, and frequently also the measurement of the concentration of, various gases, environmental pollutants, and toxic gases, is of increasing importance. While the presence and concentration of these can usually be accomplished by the use of conventional sampling and analytical techniques, many of the situations which they represent require very rapid accomplishment, and rugged and reliable devices for the purpose. It is no longer suitable occasionally to sample stack gas or ambient air and then in what was once a reasonable time to read out what the conditions were. Frequently these situations if not corrected can result in costly waste of fuel, pollution of the atmosphere which may give rise to penalties, or to the unwarned presence or emission of toxics.

As one example, operators of combustion devices such as boilers are well aware that continuous detection and measurement of gases produced in minor quantities such as carbon monoxide, and responsive control of the processes which produce them, can result in dramatically improved fuel efficiency. In such installations excess air was formerly widely used in combustion processes on the assumption that a lean mixture would assure more complete combustion of fuel. However, as combustion processes became better understood, it also became apparent that the use of excess air was wasteful, because among other things it required the flame to heat excess gas, enabled the formation of SO3 instead of merely SO2, encouraged the formation of NO, created sulfate emissions, and in some cases even increased smoke formation by shortening the flame length. Combustion operations using low excess air improve all of the above situations, but the control must be accurate, and be quickly responsive in order to insure complete combustion while avoiding uneconomical operations and the formation of excessive pollutants. The concentration of carbon monoxide produced by a combustion process turns out to be a good measure of the average combustion quality, i.e., nearness to stoichiometric conditions. For example, no CO means too much air, while high CO means not enough air.

With the realization that controls based on the concentration of some minor component of a gas stream can lead to an optimized combustion function, serious development of suitable instrumentation was undertaken, especially instrumentation for measuring the concentration of carbon monoxide in a gas stream. Of course, measuring techniques and instruments had long existed for this purpose, but frequently they relied on sampling techniques which were too slow to provide useful data for on-line adjustment of combustion parameters, or not reliable enough for continuous duty.

The increased stringency of government regulations relating to power plant emissions has long been a prod for the development of in-situ gas analyzers, and several types of such analyzers have been installed in hundreds of power plants in recent years. Some utilize the technique known as "gas filter correlation", which is a technique utilized in the instant invention. It is an object of this invention to employ this technique to better advantage in a gas analyzer whose sampling is done "in-situ", meaning without removal of a sample from the stream, but instead securing data as the consequence of measurements or observations of spectral energy which has been subjected to interaction with the gas stream itself—either by having passed through the gas stream or by having emanated from it.

Gas filter correlation is a well-known procedure which does not require description here for an understanding of the invention. A useful reference on this subject is "Analytical Methods Applied to Air Pollution Measurements" by Stevens and Herget, Chapter 10, pages 193–231, published by Ann Arbor Science, 1974, which is incorporated by reference herein for its showing of the applicable theory.

This technology, and the instrumentation provided by this invention, are not limited to applications which are sensitive to stack gases, or even only to actively flowing streams of gases. While such applications represent a very large market, there is a growing need to be aware of conditions in what may suitably be called a "bulk" presence of gases. Detection of pollutants and toxic gases in the atmosphere is another example, and an extension of this additional application is surveillance and warning of the presence of undesirable compounds or concentrations of them.

Enclosure and barrier surveillance represents a substantial potential application for this invention. For example, it is useful to know whether a landfill, dump, or even a chemical plant is emitting any specific gas or pollutant. In turn, it may be desired only to know the total emission in all directions, in which event a perimeter would be monitored, or in some specific direction in which a barrier would be monitored. In these situations, there is a "stream" of gases being monitored, although not precisely in the sense of a stack gas in which there is a rapid steady flow. Even so, the concepts of this invention are useful to both, and the term "stream" of gases defines both of them.

Gas filter correlation techniques generally utilize narrow band pass filters. In many applications of this invention, it is quite convenient to use for filters, cells containing specific gases at known and precise concentrations and pressures. These techniques are most suitable for detection and analysis of gases whose spectral absorption pattern includes a number of lines in the band of interest, and in which the "interleaved" regions are also utilized in the procedures. Such gases include carbon monoxide and hydrochloric acid.

More classical techniques are used when instead of many absorption lines within the band of interest, there is merely a wide absorption line or band. Then optical notch filters will be employed instead. Examples of such gas are hydrocarbons and sulfur dioxide.

The apparatus of this system can utilize either optical filters or gas cells, and the generic terms "filter means" and "filters" is used for both of them. In addition, the sensitivity of the instrument can be improved by providing a narrow band pass filter that limits the energy reaching the detector to those wavelengths that are of interest.

Also, while the measurement of concentration of a selected gas may be of primary interest in many installations, in others the detection of the presence of that gas may be of primary concern, therefore this invention is not intended to be limited to use with measurement devices, but also extends to surveillance and detection devices where the presence or absence of the compound is of interest.

The United States Environmental Protection Agency has a requirement to audit analyzers with reference cylinder gases for zero and span calibration. In most cases, for in-situ analyzers, this has been done by removing the analyzer from the stack to perform the calibration or audit. Removing the analyzer from the stack for system calibration is a very cumbersome, very time consuming, and annoying process.

It is therefore an object of the present invention to improve an analyzer by providing a method and apparatus for periodic zero and span calibration that does not require removal of the analyzer from the stack. This method involves the use of an audit cell as an internal in-line flow calibration cell. The use of the audit cell allows the present invention to meet Environmental Protection Agency requirements in a very simple way, with no-human interaction.

High and low frequency fluctuation in the infra-red (IR) emission from a source is a serious cause of instrument noise and drift. Previous efforts have relied on a photodiode and feedback to regulate the IR source. Such a system is disclosed and described in U.S. Pat. No. 5,457,320 of R. D. Eckles et al issued Oct. 10, 1995. The system disclosed in this patent merely controls visible emissions from the source, not the IR. Broad band IR emitters such as glow bars and hot filaments, have 16 emission profiles (i.e., photon density wavelength) similar to the ideal "black body". Reducing the power to a device increases the amount of long wave IR radiation and decreases the amount of visible "higher energy radiation". At the same time the amplitude of the entire emission pattern decreases. Therefore there are two competing effects at work which can cause complications when regulating the source using a visible detector such as a photodiode especially for high-precision work.

It is another object of the present invention to incorporate two devices to measure the energy emitted by an IR source to give a direct reading of radiation used in the measurement of the gas and by use of a feedback loop control the source output. The new system uses a narrow band optical filter and a thermopile to measure photon density and regulate the output of an IR source with a feedback loop that is more efficient than previous sources to allow precision work to be carried out with the instrument.

It is still another object of the present invention to provide an audit cell for calibration across a gas stream, without requiring the analyzer to be removed from the stack, that uses isotopically labeled gases to extend the analyzer dynamic range, simplify calibration, and reduce interference. Since the instrument can never duplicate the gas stream optical path length internally in the analyzer an audit cell having a shorter optical path and higher concentration of preference gas so that the product of concentration times the optical path length is identical in the audit cell and the gas stream of the stack works for most gases. For very large stacks it may be impossible to have a concentration sufficient for calibration. For this purpose a calibration "trick" of measuring stable isotopically labeled gases in the path is used. These gases also have a distinctive and measurable absorption (or emission) spectra. Thus isotopically labeled gases at much lower concentration that may be as low as 1% of the principal gas concentration can be used to calibrate the instrument.

Personal computers and personal computer architecture have becomelextremely popular in both general purpose and dedicated applications however their use is limited due to the large size of the motherboard and expansion cards. Thus a specification, both mechanical and electrical, has been conceived to optimize computers for use where the large size personal computer option is not viable. This specification is known in the art as PC/104 architecture. By using this architecture the form factor or dimensions of the computer have been reduced to less than four inches square and eliminates the means for back planes, card cages, by using a self-stacking bus. The system also minimizes component power consumption by reducing required bus drive power of most signals.

It is therefore another object of the present invention to adapt PC/104 bus architecture to allow an onboard computers for instrument control. In applications where the onboard PC/104 architecture is not possible, the computer will be remote and the stack-mounted analyzer will consist of an optical head with a series of serial modules used to send signals to a remote computer. A PCB may be used at the stack-mounted analyzer to allow the use of Ethernet instead of serial communication. Either way, digital signals will be sent to a remote PC.

Still another object of the present invention is to provide onboard electronics and monitoring system in the form of a computer having a PC/104 form factor. This allows the use of an onboard computer in the analyzer that conforms to the PC/104 specification including both mechanical and electrical specifications and permits a highly rugged and miniature computer to be used on- board the in-situ gas analyzer.

When the term "gas" is used herein, relating to the substance being detected or measured, it is not intended to be limited to compounds in their gaseous state. The measurement or detection of opacity is also comprehended, and this may involve the detection and measurements of particulate conveyed in a gas stream. Such a situation is also intended to be included in the term "gas".

It is an object of this invention to provide a system which can have a direct zero and span measurement, even with gases flowing or present in the apparatus; which can readily and automatically be calibrated, and all interferences automatically rejected; which can be constructed so as readily to be accessed for routine repair and maintenance, and even deposed at a considerable distance from the situs being sampled or observed; which is sufficiently heat resistant that its readings do not stray during temperature excursions; which rejects spurious signals from its surroundings; and which is forgiving of substantial physical shifts and changes in the physical environment, such as by dimensional expansion and contraction.

Still further objects are to provide better techniques for internal calibration of the instrument, for more efficient optical path, and for decreased sensitivity to external physical distortions such as vibratory and temperature induced dimensional shifts.

BRIEF DESCRIPTION OF THE INVENTION

Apparatus according to this invention utilizes spectral energy which has been subjected to interaction with a gas either by having passed through the gas, or by having emanated from it and uses a unique internal audit cell for system calibration.

The present invention is an improvement to the invention disclosed and described in U.S. Pat. No. 4,632,563 issued Dec. 30, 1986 and U.S. Pat. No. 4,746,218 issued May 24, 1988 to Harry C. Lord.

The heart of this invention is a new and improved analyzer with an array of filter means for reference and optionally for calibration, to which a beam of spectral energy is directed. The beam will, before or after interaction with these filters, also interact with the gas, either by being passed through the gas, or by having emanated from it. A detector is responsive to the energy which has interacted both with the gas and with the reference filters (optionally also with the calibration filters).

In one embodiment, the analyzer operates within itself to direct the energy to be analyzed to selected filters, but can be placed anywhere that it receives an incoming beam segment, which can be fixed, or where it can produce a beam to be passed to the gas, which beam can also be fixed. Optional means can be provided to present different filters to the beam from time to time.

Optical devices can be placed in the path of the beam at appropriate locations to exert a focusing action which assures that regardless of physical shifts or movements of reasonable magnitude, the beam will fully fall into-the face of the detector. In other portions of the system, a split-aperture Cassegrainean telescope which both projects the beam and receives the returned beam, or a lens system, or cube corner reflectors can be provided which also reduce sensitivity to dimensional variations.

In one application, a spectral source provides a beam which is passed twice through a stream of the gas (being reflected after the first pass). Alternatively, the source for one of the fixed beams may be emissions from the process or from the gases themselves.

In another application, the spectral beam may be passed a single time through the stack, and then received and treated by the analyzer. This embodiment may also be adapted to receive and treat a beam of energy derived directly from the gas itself, by emission, or by "observing" the process itself, such as by receiving energy from a process flame in a burner, or from the gaseous region above a process, such as just above the molten glass surface in a glass furnace.

In still another applications, the beam path traverses a boundary or a barrier just above the ground. This enables a detection or surveillance type operation.

Generally, infra-red energy will be utilized with this invention. Gases of frequent concern have useful absorption patterns in the infra-red region. Furthermore, infra-red radiation can conveniently be emitted or collected. However, visible and ultra-violet energy may also be used advantageously in some applications. The invention is not intended to be limited to one in which only infra-red radiation is utilized. Of course, filters respective to the wavelengths being employed will be employed in place of these which are respective to infra-red radiation.

When reference cells are used for filters, they can contain mixed gases to measure parameters of more than one gas, whose pertinent spectra do not interfere with one another. Carbon monoxide and sulfur dioxide constitute one such mixture.

According to yet another preferred but optional feature of the invention, a chopper is placed in the energy path, whereby to provide pulses of energy to the detector at a frequency determined by the chopper, thereby providing means to reject spurious data.

According to yet another preferred but optional feature of this invention, a separate calibration beam path is provided which by-passes the stream on its way to the analyzer in order to give a zero-based reading.

According to-still another preferred but optional feature of the invention, a pair of cube-corner retro-reflectors are provided to return the beam, one on each side of the gas stream, one to return the beam across the stream, and the other to return it in the calibration mode without crossing the gas stream.

According to yet another preferred but optional feature of the invention, gas cells used for calibration have two separate gas chambers containing gases at different concentrations and pressures in order to provide two sets of data for the solution of two simultaneous equations.

In still another preferred but optional feature of the invention an audit cell is provided for in-situ zero system calibration. The use of an audit cell permits the calculation of an accurate zero and span calibration points. An incremental additions method is used in conjunction with the audit cell for modeling the instrument zero. The preference gas is added to the audit cell in a concentration that has a pre-determined ratio to the gas being analyzed and the optical path length employed in the measurement. The audit cell is placed in series with the instrument and concentrations of a reference gas are incrementally added. By knowing what the concentration of the reference gas is inside the audit cell, a zero can be retroactively calculated that is much more accurate than what is normally generated by using a zero mirror in the instrument, which includes correction for any interferences from other interfering gases present in the gas stream.

Also in another preferred embodiment of the invention the reference gas is isotopically labeled with a lower abundance stable naturally occurring isotope of one of the elements of the gas; e.g. $^{18}O$ instead of $^{16}O$ to allow calibration where a direct ratio of reference gas to the stack gas is not possible. Use of an isotopically labeled preference gas can reduce the amount of concentration needed to 1% times the concentration ratio in some cases, or less.

The use of the audit cell allows the duplication of the optical path length internally in the analyzer by using the higher concentration of the preference gas so that the product of the concentration times the optical path length is identical in the audit cell and in the stack. This method works for most gases and for all gases that will be measured in the ppm or ppb levels.

However, for measuring and calibrating a gas at 10% like carbon dioxide ($CO_2$) for example in a stack that is 30 foot wide, in a double-pass system the optical path length is twice the stack diameter which is 60 feet. Thus, you would require 600% feet. If you have a one foot audit cell, you would have to have 600% of the preference gas in the audit cell which is impossible. It was recognized that oxygen has suitable isotopes, for example $^{18}O$, and carbon has a suitable isotope, for example $^{13}C$, each of which is only a small percent of the primary naturally occurring isotope(s). Furthermore the absorption spectra for the molecule with the different isotope(s) is unique and hence may be used for the measurement. When you measure the 10% $Co_2$ if the instrument looks specifically at $^{13}CO_2$, the concentration is now only 1% times the inverse ratio of optical path length to cell length and now it is at 6% feet and the audit cell can now be easily filled with calibration gas. Thus, by isotopically labeling reference gases in the audit cell, the system can perform a calibration trick using a much lower concentration.

Another important aspect and optional feature and improvement in the invention is the use of a feedback loop for an IR source control. The improved system described herein uses two devices to measure energy emitted by the IR source. A narrow band pass optical filter (NBOF) to isolate a specific spectrum window and the thermopile to measure the photon density of radiation. The advantage of this configuration is that the NBOF can be used to isolate the same spectral window as the one in the measurement of the gas by the instrument (e.g., $2,100 \pm 25$ $cm^{-1}$ for carbon monoxide). With this approach the thermopile gives a direct reading of radiation used in the measurement of gas rather than an indirect measurement that might be obtained by use of a visible radiation detector such as a photodiode. This regulation of the IR source using the analyzer computer and a feedback loop from a narrow band optical filter and thermopile is more efficient than previous versions thereby allowing ultra-high precision work to be carried out with the instrument.

Still another optional feature and improvement of the analyzer disclosed herein is the use of improved instrument configuration such as an on-board computer. The on-board configuration for the computer or PC for application where the process and environment and conditions allow is a PC/104 architecture or form factor. The PC/104 form factor is highly rugged and miniaturized, since it has no back plane board and yet has not been presently used for industrial in-situ gas analyzers. The use of the PC/104 form factor permits the PC to be incorporated into the analyzer because it has a configuration that can be fit in a space of less than four inches square.

The analyzer uses an IR detector mounted on a pre-amplifier board which relies on a low noise field effect transistor (FET) operational amplifier to make detector noise a limiting performance factor. A separate feedback loop controls the detector temperature within plus or minus 0.005° C. or better.

The system and circuit is also designed to accommodate a variety of detector types for detection of a wide range of spectral wavelengths from below 0.5 $\mu$m to above 20 $\mu$m with increased sensitivity. Little or no change to the signal processing electronics is required for swapping detectors making this a powerful modular system. The system described allows important environmental gases (e.g., H2SO4, SO3, NH3) to be measured reliably in an industrial environment for the first time. A signal processing board is mounted on a chassis known as a PC/104 stack and receives a signal from the pre-amplifier board. Temperature and pressure control loops are managed by an additional board mounted on the PC/104 stack. Files can be accessed and transferred remotely using off-the-shelf remote access software.

The above and other features of this invention will be fully understood from the following detailed description and the accompanying drawings, in which:

BRIEF DESCRIPTION OF THE DRAWINGS

FIG. 4 is a partially schematic axial view of the presently preferred embodiment of the invention, when operating in the double-pass mode;

FIG. 7 shows an alternate means to present various cells;

FIG. 8 is an example of a cross-section taken at line 10—10 in FIG. 7 showing four cells.

FIG. 9 is a fragmentary enlargement of part of FIG. 4;

FIG. 10 shows an alternate sampling technique, with the audit cell external to the analyzer;

FIG. 11 shows a convenient means for mounting filters;

FIG. 12 is a cross-section taken at line 12—12 in FIG. 11;

FIG. 13 is a modification of the system including the filter of FIG. 12;

FIG. 14 shows gas cell substituted for the interference filter of FIG. 12;

FIG. 15 shows the invention used for perimeter surveillance;

FIG. 16 is a side view of FIG. 15;

FIG. 17 shows the system used for barrier surveillance; and

DETAILED DESCRIPTION OF THE INVENTION

Figure 5:
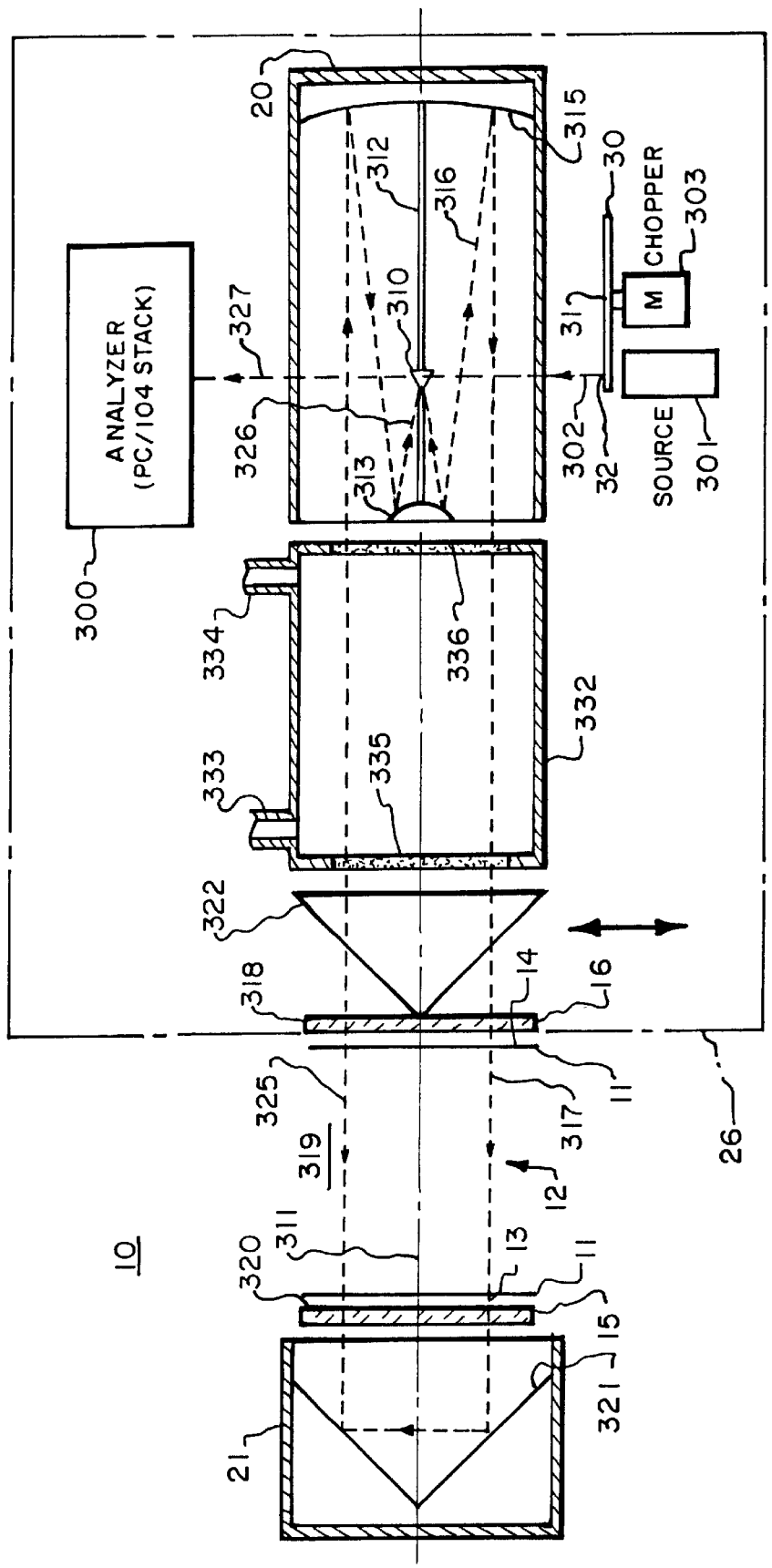
FIG. 5 is a partially-schematic axial view of a modification of the presently preferred embodiment of the invention, wherein the audit cell has been inserted into the optical beam.

FIGS. 4 and 5 show an illustrative and useful embodiment of this invention, installed so as to measure the concentration of a selected gas in a gas stream. This example is a doublepass instrument, the beam passing twice through the gas being sampled. In the example given, the gas being observed is carbon monoxide. However, any other gas or substance subject to spectroscopic analysis could instead be detected and measured by appropriate modification of the instrument. Therefore, the scope of this invention is not to be limited to carbon monoxide analysis.

A gas stream containing carbon monoxide (or other gas whose concentration or pressure is to be measured or detected) passes through a conduit such as a duct or a stack 10 (shown schematically) from a combustion device such as a boiler (not shown), on its way to atmosphere. Such a conduit will have a continuous peripheral wall 11 through which the sample gas stream 12 flows.

This invention is not limited to use with gas streams in stacks or ducts. Such an example is given to show the one mode contemplated for its use at the present time. It is also applicable to observation of gases at the situs of the process, such as by analyzing spectra from the process itself. An example is a flame, directly observed. Another example is the observation of the gaseous region above a process, for example, above the glass surface in a glass furnace. Still other examples are the sampling of the atmosphere generally, or of gases emanating from a site, or passing a barrier. And still another is to analyze the gases from a vehicle as it passes through the light beam.

Two ports 13, 14 are formed through the wall of the duct, and respective windows 15, 16 are placed in them to provide observation access for the instrument. The window glass should not be absorptive of wavelengths of interest. For carbon monoxide analysis, sapphire glass is suitable.

The windows are accessible so they can be cleaned. Because they are frequently located at inconvenient locations, means can be provided to increase the length of time between cleanings. One such means is a nozzle manifold placed adjacent to, and just upstream from, the window. Air blown out of these nozzles forms a region of increased pressure along the surface of the window, thereby isolating the window from materials in the stream which might adhere to the window and reduce the transmission. Ultimately the window could become excessively soiled and then would have to be cleaned, but much less frequently than if this feature is not provided.

A transceiver module 20 is mounted to the conduit wall (for example, adjacent to one of the windows). A reflector module 21 is mounted to the stack wall adjacent to the other window. If preferred, the windows can be formed as part of the modules, and can be reached for cleaning by backing the modules away from the stack wall.

An emitter 301 of spectral energy, in this case a source of infra-red energy in the band range between about 0.5 μm and 20 μm, is mounted to housing 26. The presently preferred emitter is a cartridge heater, but one alternate source might be a conventional home appliance igniter, or any other stable source of infrared radiation. Such igniters are inexpensive and durable. Despite the fact that they were designed for intermittent usage, they perform very satisfactorily over a long term of continuous use, glowing a dull red color, and emitting infra-red energy in the said band which is useful for infra-red spectroscopy.

To provide a pulsed beam, a rotating chopper wheel 30 is rotatably mounted in a path of the energy from the source. The wheel is driven by a motor 303 at a rotational velocity which will produce pulses of the correct frequency. The wheel has an opaque structure 31, with transmissive portions 32 through the structure. These portions may conveniently be open slots, open at the edge of the structure. Their number and width is selected so that, with a selected rotational velocity, energy pulses of the correct duration and frequency pass through the wheel.

A divergent beam 302 of infra-red energy leaves the chopper wheel, and impinges on a front surface mirrored prism 310.

This analyzer is adapted to use gas filter correlation spectroscopy. In this technology an energy beam is passed through a correlation gas cell (at a separate time), instead of through a reference gas cell when it passes through the detector, and at another time through a reference gas cell. Thus, one of cells 328–331 (FIG. 8), say cell 328, is a correlation cell, and another cell, say cell 329 is a reference cell. Cells 330 and 331 are for the measurement of another gas.

In the typical gas filter correlation instrument, a leak in the correlation cell results in a change in absorption at the line centers, causing a change in the instrument drift. As described below, this instrument uses multiple gas cells with fixed and known relationship one to another. The electronics automatically check this relationship and compensate, and can be instrumented to alarm if one cell has changed relative to the others.

Across-the-stack instruments, with or without a cross-stack pipe or other rigid support, have demonstrated sensitivity to alignment changes. As the sun shines on one side of the stack, or when process parameters change, temperature changes in the stack or duct wall cause differential movement of one side relative to the other. The optional components for the instant system (mirrors and lenses, especially the lenses in the analyzer) can correct for these variations, when they are designed with these variations in mind.

The power supplies and the stepper motor control, and other functions, can be located on a single printed circuit board below the optical base plate. The output of the optical head can be transmitted either by analog or digital means to a remote panel.

A microprocessor is used for signal processing. This includes setting the optical path length across the stack, full scale of the instrument, linearization of the output, automatic calibration, temperature compensation of the date (through the input of a thermocouple readout in the gas stream), pressure compensation, adjustable high and low limit alarms, and diagnostics including power failure, blower failure, source failure, detector failure, stepper motor failure, leak in a gas cell, dirty window, high temperature alarm for the detector, high temperature alarm for the instrument box, and electronics failure, as explained.

The instrument box, the reflector box, and the associated air purge blowers and filters, as well as the junction box for power in the signals out can all be enclosed in a weathertight enclosure for basic instrument weather protection.

Yet another way to remove the more sensitive elements of the device to a more favorable environment is shown in FIG. 7. The instrument is responsive to infra-red beams that have passed through or which have emanated from the gas stream. While it is good practice to place the instrument near to the surfaces it measures or reacts to, sometimes this is inconvenient. Electronic transmission of the raw data also involves problems.

Figure 3:
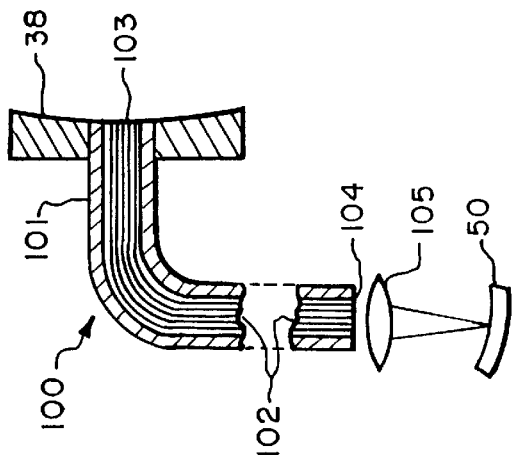
FIG. 3 is a fragmentary schematic view showing means for placing the instrumentation at a greater distance from the gas stream, for example by including fiber optics.
Figure 6:
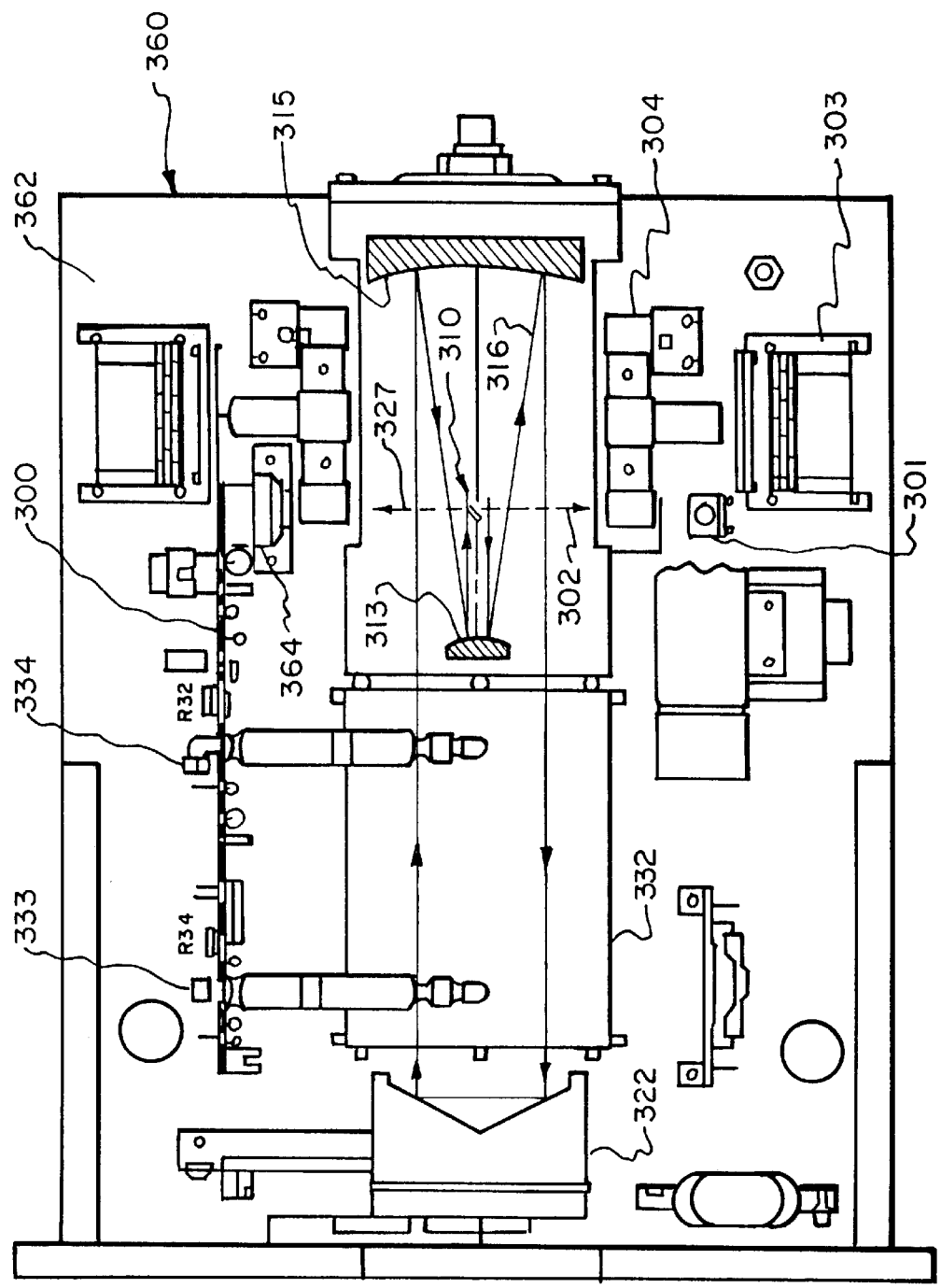
FIG. 6 is a top view of the transceiver illustrating the modular construction and addition of the modification shown in FIG. 5.

This invention provides the advantage that the optical system can be interrupted at various places, and coupled by optical forwarding means of various types. The presently-preferred such optical forwarding means is a fiber optic bundle. This is shown in FIG. 3, where a typical fiber-optic bundle 100 having a sheath 101 and a large number of glass fibers 102 have one of its ends 103 fitted in the aperture in place of the detector 364 (FIG. 6). Its bundle receives energy from beam 327. The fibers conduct this energy to end 104, and a focusing lens 105 focuses it onto initial mirror 50, wherever it is placed. The bundle can be bent and can be of any length so that result is to enable the deflector and cells to be placed more conveniently for the user. The glass fibers will be coated with an initially reflecting coating in accordance with known fiber-optics techniques.

Other optical forwarding means can be used instead. An example is the classical rod-lens telescope shown in Hopkins U.S. Pat. No. 3,257,902. However, this device does not readily accommodate bends, and may be more difficult to employ. It does have image-forming properties superior to those of fiber glass bundles, even of coherent fiber bundles, should image properties be of interest.

Figure 1:
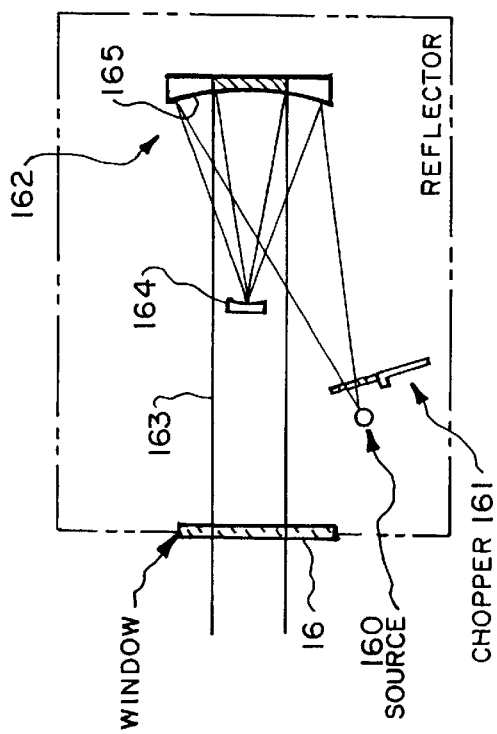
FIG. 1 is a fragmentary view of one embodiment of the invention.
Figure 2:
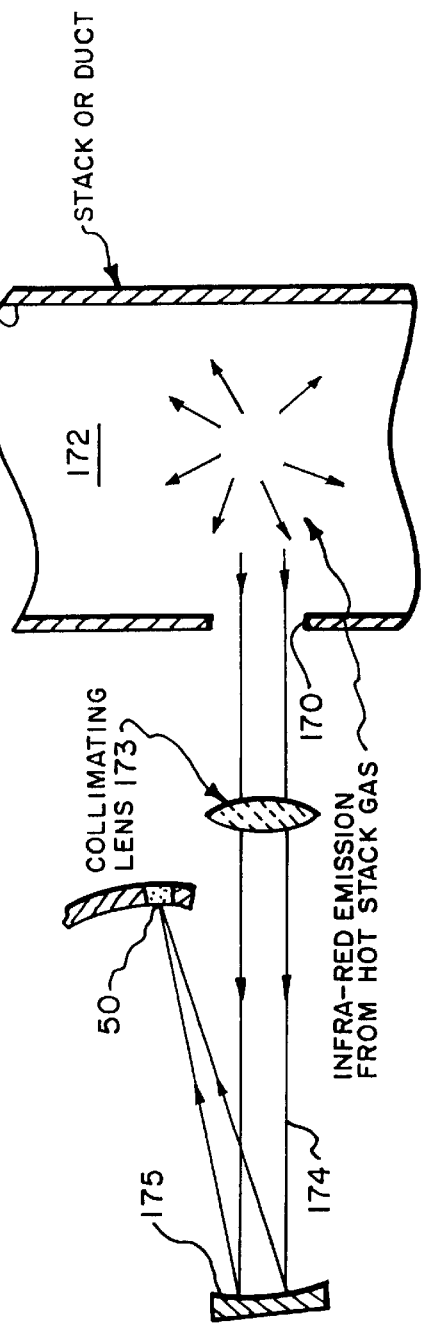
FIG. 2 is a fragmentary view of another embodiment of the invention.

The embodiment of FIGS. 1 and 2 is characterized as a double pass system. In a double pass system, the beam is twice subjected to the effects of the gas stream, having been directed through it, and then reflected back through it again. FIG. 4 shows the presently preferred embodiment of the invention. It enables the available radiant energy more efficiently to be used, and the instrument to be less sensitive to external distortive forces, in addition to other advantages.

FIG. 1 illustrates one embodiment of an optical design, where the light from the source 160, is chopped by chopper 161, and collected by the primary mirror 165, to a secondary mirror 165, back to the primary mirror 165, and then projected as a collimated beam 163 through window 16. Window 16 serves as a gas tight seal the enclosure housing this optical projection system 162.

The objective of the system is, as before, to provide to an analyzer 300, a beam which has passed or will pass through a gas sample, or cells ("filters). There are other viable analyzers as will later be shown.

An infra-red source 301 emits infra-red energy along path segment 302. A chopper 303, which conveniently comprises a bidirectionally rotatable notched disc 304 is in said path. The spacing of the notches and the speed of rotation of the disc determine the chopping frequency. 900 Hz is a useful frequency for certain mid-IR detectors, when this device is used to screen out background noise and interference.

A two element deflector mirror 310 is disposed on the central axis 311 of the optical system. A baffle 312 extends axially along the system to divide it into two halves. It occludes path segment 302, and is divided into two elements by mirror 310, and focal mirror 313.

Mirror 310 has a first reflective element 310a (FIG. 9) which reflects rays along segment 302 to focal mirror 313. Element 310a will direct the rays to domed focal mirror 313. Domed mirror 313 will direct the impinging rays onto cassegrainean mirror 315 along path 316 which in turn will reflect them along a collimated path 317, which is half-tubular, axially.

Path 317 exits through window 318, crosses stack 319, passes through window 320, and impinges on a trihedral retroreflector 321. This is a classical cube-corner reflector comprised of three mutually perpendicular mirrors. The beam represented by path 317 is therefore rotated 180 degrees, and displaced to the other side of the plane defined by baffle 312. The rays are returned precisely parallel, along path 325 and impinges on the other half of the Cassergrainean mirror 315, which in turn reflects them to the other part of the focal mirror 313, which in turn reflects them along path 326 to the other side of deflector mirror 310. The shape of element 310b is such as to direct the rays in a path 327 to analyzer 300. Rays in path 327 can be treated precisely as in FIGS. 1–7.

As before it is necessary to have an optical path which does not include the sample in order to provide for calibration. In this embodiment, this objective is readily met by providing a second retroreflector 322 between the Cassegrainean mirror and stack. This retroreflector is identical to retroreflector 321. It may be placed in the way of path 317, and will return the rays on that portion of path 325 which does not include the sample. The second retroreflector can be mounted in such a way to be removed manually or automatically when not desired. This is an elegant means to provide two effective paths, with all of the advantages available to both.

A selectively rotatable wheel 350 in FIG. 7 or wheel 400 in FIG. 11 contain filters for calibration. These filters can be gas cells, optical filters, or other means to reduce the transmitted energy by a fixed and reproducible amount at the wavelength being measured, as preferred. This wheel will have void regions to pass beam 302, and can move the appropriate filter or filters into the path of this beam.

FIG. 2 utilizes emission spectroscopy instead of absorption spectroscopy in the equivalent of a single pass system. A window 170 (FIG. 2) in the wall of a duct 171 for a gas stream 172 that emanates infra-red energy passes energy to a collimating lens 173 that forms a beam 174 which impinges on a focusing mirror 175 (which is equivalent to mirror 315 in FIG. 4). This beam is reflected to mirror 313, and is treated by the remainder of the system of FIG. 4. The chopper (not shown) can be placed in the path of the beam.

For calibration, the separate calibration system shown in FIG. 6 can be provided. In all embodiments, when changing from a calibration to an active measuring mode, appropriate shutters will be moved to exclude confusing or extraneous beams from the system. Some of these are not shown, because their purpose and possible locations are evident.

Gas cells (sometimes called "filters") useful in the analyzer and in the system, and their use, will now be described. In one embodiment, shown in FIG. 7 Cell 330 is referred to as a "correlation" cell. Cell 328 is referred to as a "reference" cell. A second set of cells are mounted in turret 304 (FIG. 6) on the source side as "calibration" cells.

Cell 400 (FIG. 14) has a single gas-tight compartment 409. It contains gas of the type being measured, for example carbon monoxide at a partial pressure of generally the same partial pressure as the substance exists in the sample being measured, and another gas as a broadening agent, for example, nitrogen. This other gas increases the total pressure in the compartment 419 to a pressure that is sub-atmospheric, and such that the line widths in the spectrum from this cell in use will be about the same as the line widths in the spectrum from the sample in the process being measured. In use, correlation cell 400 provides a measurement of background intensity.

Reference cell 328 might be simply open to the air, or might have an identical single gas-tight compartment 409.

Broadly stated, the filling of correlation cell 409 is such that the absorption line widths in the correlation cell, which is at the ambient temperature of the instrument box, are essentially identical to the line widths in the gas stream containing the sample. Applications for this instrument for analyzing hot gases will normally range from gas stream temperature of about 250° F. up to about 750° F. Applications outside of this temperature range are also possible, for example, ordinary ambient temperatures when conditions at or near the surface are being surveyed or measured. Sufficient absorbing gas partial pressure is utilized in the correlation cell to insure essentially complete absorption of the line centers at those wavelengths where the sample gas absorbs. With a narrow band pass filter in front of the detector which transmits energy only in wavelength band (A) where the sample absorbs, then the only energy seen by the detector when the correlation cell is in the beams, is that energy which is transmitted through the gas stream at those interleaving wavelengths where the sample does not absorb.

The reference cell will be filled to a higher total pressure such as five (5) atmospheres. This causes absorption at the same wavelengths, but because of the higher total pressure the absorbing lines are much broader. The detector then alternately sees a beam which passes through the correlation cell with complete absorption of sample, giving only the background radiation, and then the beam which has passed through the reference cell, giving the background radiation plus a partial absorption of CO (caused by the CO in the stream and in the cell). Since the background is the same through both cells, the change in absorption by the sample in the reference cell is directly proportional to the concentration of the sample in the gas stream.

The calibration cells provide an up-scale instrument calibration point. With the zero and span information, a microprocessor based set of electronics can provide a periodic automatic full calibration and output adjust in accordance with known procedures.

As part of a calibration cycle, the sample beam may be sequentially stepped through either one or in some instances each of two calibration cells. The use of two cells in series with the unknown sample gas concentration provides two incrementally added known concentrations to the unknown process concentration. These two additional data points allow the computation and elimination of zero and span offsets. For example, in the measurement of CO, there might be an interference from H2O and/or $CO_2$, depending upon the bandpass filter specifications. This calibration cycle may be done frequently, at a selected frequency, which may be adjustable. Five minute intervals are generally satisfactory.

A unique method for in-situ calibration is illustrated in FIG. 5. The addition of audit cell 332 for calibration across the stream 319 eliminates the requirement for removing the analyzer for the stack for calibration. The United States Environmental Protection Agency (EPA) has a requirement to audit the analyzer with the reference cylinder gas for the gas being measured. The system shown in FIG. 5 is already designed with internal zero retro-reflector 322 for periodic zero calibration. To provide in-situ calibration audit cell 332 normally filled with nitrogen because nitrogen does not absorb infra-red radiation is inserted between internal retro-reflector 322 and domed focal mirror 313. Audit cell 332 has windows 335 and 336 for passing optical beams 317 and 325. Audit cell 332 acts like a window or clear aperture and also provides a system zero when retro-reflector 332 is in the beam. When retro-reflector 332 is out of the beam, because audit cell 332 does not absorb any energy, the light beam simply passes through windows 335 and 336 and measures what is in the stack. Audit cell 332 is provided with inlet 333 and outlet 334 for adding reference gases. When it is time to calibrate the analyzer with cylinder gas, the system does not have to be removed from the stack but can be calibrated in place (in-situ) by bringing retro-reflector or zero mirror 322 in and activating a solenoid to flow calibration gases into and through audit cell 332 through inlet 333 and outlet 334. The system can now meet EPA requirements very easily without the complicated task of actually removing the system from the stack to perform calibration. Such a task is very cumbersome, time consuming, and an annoying process. The unique feature of the audit cell is there is no need for any manual interference so the analyzer is not disturbed when one of the calibration checks is made. The system is unique and novel and allows EPA requirements to be met in a very simple calibration method that requires no human intervention. Such a device can be very effective because it can operate automatically. In addition, these systems are being used more and more often in open path applications, such as for remote vehicle exhaust monitoring.

A very unique feature of audit cell 332 in the in-situ analyzer is how an accurate zero is obtained. The way zero is normally obtained is by measuring the internal zero inside the analyzer, with the internal mirror optically isolating the transceiver from the stack. However, that only affords an approximate representation of what zero would be with the stack there as well because of various optical effects. These result from: lensing effects due to the high temperature of the gases in the stack, particles in the gas stream, alignment shifts of the stack and mounting hardware, condensation and particles building up on the windows. All these effects need to be integrated into the zero measurement. The real zero is not a theoretical zero but is calculated based on the internal zero of the instrument and with the audit cell there is now a way to calculate a real zero.

To perform or make a determination of an accurate zero the system measures across the stack with the retro-reflective mirror 332 out and the audit cell in place in series with the instrument between domed mirror 313 and window 318. Concentrations of a reference or particular gas are incrementally added to audit cell 332. By knowing the concentration of the reference gas inside audit cell 332 and assuming the concentration of measured gas does not vary inside the stack in the short period required to make the measurement, the system can retroactively calculate a zero that is much more accurate than what would normally be generated having retroreflector 322 in. This is a unique, new feature that has not ever been used in any known instrument.

Figure 19:
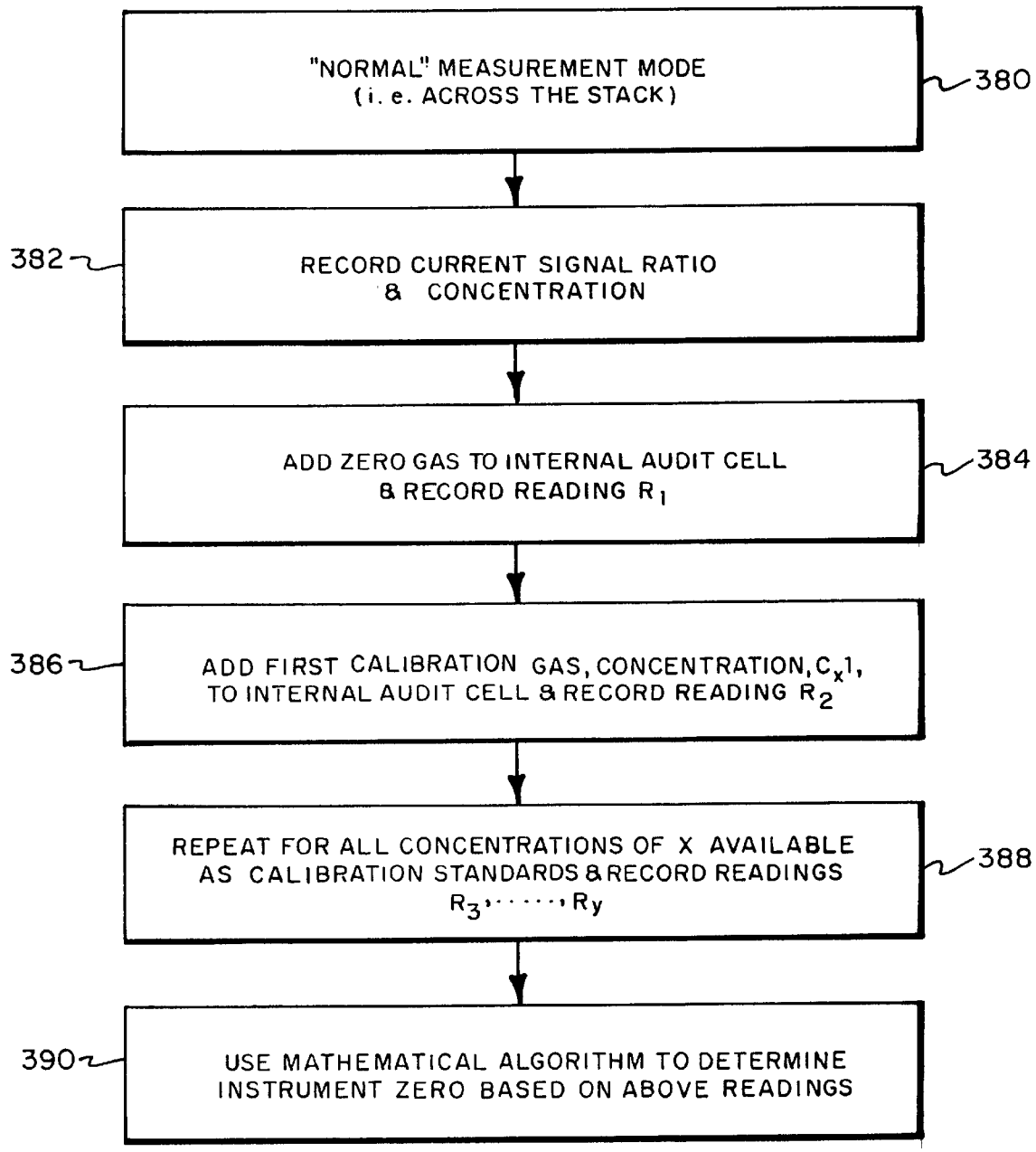
FIG. 19 is a flow diagram illustrating an incremental additions method for modeling the instrument zero.

The system uses an incremental additions method for modeling instrument zero. This method is illustrated in the flow diagram of FIG. 19. The start position is with the system in the "normal" measurement mode 380 for taking measurements of the analyte "x" across the stack. The next step is recording current signal ratio, defined as a ratio of the measurement signal to the reference signal or the difference between the measurement and reference signals divided by the sum of the measurement and reference signals, and concentration 382. The incremental addition of concentrations of a preference gas then begins with the step 384 of adding zero gas to internal audit cell and record reading R1. Next is the addition of the first calibration gas 386 at a concentration Cx1 to audit cell 332 and record reading R2. The next step 388 is to repeat all concentrations of analyte "x" available as calibration steps and record readings R3 . . . RY. The final step 390 is to use a mathematical algorithm step to determine instrument zero based on the readings R1 through RY. This algorithm is developed specific for each instance and is a function of the analyte's signal Ratio, calibration curve and the optical path length.

The cylinder gas concentrations for analyte "x" being measured should include two or more calibration standards evenly spaced throughout the instrument range. The algorithm used to determine instrument zero from the R1 through RY measurement consist of an iterative regression. An important component of the model consists of instrument calibration determined experimentally when the system is built. It also can be determined theoretically mainly for species where unsuitable calibration standards are available (e.g., $H_2SO_4$). The curve consists of a plot of:

$$[x] * OPL \text{ vs } SR$$

Where, [x] is a concentration of analyte "x";
OPL is the Optical Pathlength of the air column under analysis;
SR is the instrument response as defined above.

The employed optical pathlength (OPL) is the sum of the stack diameter SD and the audit cell 332 internal length IL (i.e., SD+IL) multiplied by two as the IR beam makes two passes through this medium. The concentration of analyte "x" in the air column under analysis is $CF_n + S_x$. The principal assumption is that $S_x$ does not vary significantly (+2% of full-scale) during calibration. Varying $Cn_X$ while keeping SD, IL, and $S_x$ constant allows $S_x$ ($C_x^1$ equal to zero ppm) to be calculated accurately. Based on $S_x$ and the instrument calibration curve analyte "x", the instrument zero can be calculated. Instrument response and calibration curve can be pressure (P) and temperature (T) compensated. Corresponding P and T terms are then added to the algorithm for CnS and $S_x$. This procedure is repeated for all analytes that are to be measured by the system.

Another unique aspect of the invention is the extension of the analyzer dynamic range by using isotopically labeled gases. This method is unique and can simplify calibration and reduce interferences. With very large diameter stacks, the absorption of light by molecules in the gas is proportional to an exponential function which has as its components both the concentration and the optical path length. The optical path length, of course, can never be duplicated in the analyzer therefore we use a shorter optical path length and a higher concentration so the product of the concentration times optical path length is identical in audit cell 332 as in the gas stream of the stack and works for most gases. In fact it works for all gases that are measured in the ppm or ppb levels.

However when you need to measure and calibrate a gas at 10% such as $CO_2$ for example and the stack is 30 feet wide, this means the optical path is 60 feet wide or two times the width of the stack. For example for a stack 30 feet wide, the optical path would be 60 feet. In such cases, the main band (e.g. 2380 cm$^{-1}$ for $^{12}CO_2$) is too intense and would lead to absorption saturation and non-linearities in response. Therefore, the instrument would use narrow band pass optical filter 374 (NBOF) tuned to a band arising from a less abundant isotope, such as $^{13}CO_2$ at 2270 cm$^{-1}$ to carry out the measurement. The lower levels of this isotope avoid absorption saturation and yield good instrument linearity. For such large stacks like this an "isotopic enrichment" method is used in audit cell 332. The reason for this is that a reference gas concentration proportional to the stack cannot be used because the amount needed is in proportion to the ratio of the audit cell to the optical path through the stack.

For example, for the stack referred above that is 30 feet wide, the optical path is 60 feet and if you want to measure and calibrate $CO_2$ gas of 10% then you would need a percentage concentration of reference gas in a one foot audit cell of sixty times 10% (i.e., 60 foot optical path divided by one foot cell path) or 600% which is impossible. Therefore, a unique calibration method or "trick" of isotopic enrichment to make the calibration possible is used. This method was conceived from the recognition that carbon and oxygen, for example, have multiple stable isotopes such as $^{13}C$ and $^{18}O$. Since these isotopes are a small percentage of the predominant natural occurring isotope(s) of the elements, this isotopic enrichment can be used to allow a much higher concentration to be measured. By using isotopic enrichment in audit cell 332 and looking specifically for $^{13}CO_2$ when calibrating for measurement of 10% carbon dioxide ($CO_2$) only 1% of the 600% concentration, or 6%, is needed and a calibration can be performed. Thus by using an isotopically labeled gas an accurate in-situ calibration can be made with audit cell 332. Thus for in a 30 foot stack of 10% carbon dioxide or $CO_2$, audit cell 332 is isotopically enriched through inlet 332 and outlet 334 to produce a 6% concentration and a calibration can now be made. This method effectively and elegantly gets around the problem of having a product of path length times concentration that would require an extremely large audit cell or is impossible to met altogether.

An important aspect of the invention is the adaptation for using an on-board computer for applications where the process environment and conditions allow for on-board instrument control. For this purpose the analyzer for processing electronics 300 employs a PC/104 stack architecture. The PC/104 architecture standard is a rugged miniaturization of all standard personal computer functions. While personal computer architectures have become extremely popular in both general purpose and dedicated applications, their use in embedded micro-computer applications has been limited due to the large size of motherboards and expansion cards. For this reason the PC/104 architecture standard has been developed, with mechanical and electrical specifications that provide a compact version of the standard PC optimized for the unique requirements of embedded system applications. Analyzer processing 300 can be performed in-situ by using a ruggedized PC/104 architecture standard or form factor and also permits a unique modular construction providing distinct advantages over any prior art systems.

The transceiver of the system using processing electronics 300 and audit cell 332 is illustrated in FIG. 6. Transceiver 360 has a chassis 362 that is lengthened, compared to the previous embodiment of the invention, to provide room for audit cell 332 having inlet 333 and outlet 334. Audit cell 332 is in line with domed mirror 313 and zero systems retroreflector 332. The PC/104 architecture standard for processing electronics in analyzer 300 provides a miniaturized version without a back plane or mother board; all PCBs (printed circuit boards) plug into each other in a modular fashion using a rugged connector. It is a unique configuration that has not been used in this type of system before.

This circuit design and use of PC/104 architecture allows the system to accommodate a variety of detector types. The detector is mounted on a pre-amplifier board which relies on low noise field effect transistor (FET) operational amplifier to make detector noise a limiting performance factor. The system also contains a feedback loop that controls detector temperature to within +0.005 Deg.C (Celsius) or better.

The system shown in FIG. 6 is designed to accommodate a variety of detector types (e.g., lead sulfide, lead selenide, mercury-cadmium-telluride, indium antimonide, indium-gallium arsenide, silicon, etc.) for detection of a wide range of spectral wavelengths (below 0.2 μm to above 20 μm) with increased sensitivity. Little or no change to the signal processing electronics approach shown in FIG. 6 is required for swapping detectors making this a powerful modular system. This allows important environmental gases (e.g., $H_2SO_4$, $SO_3$, $NH_3$) to be measured reliably in an industrial environment for the first time.

Figure 18:
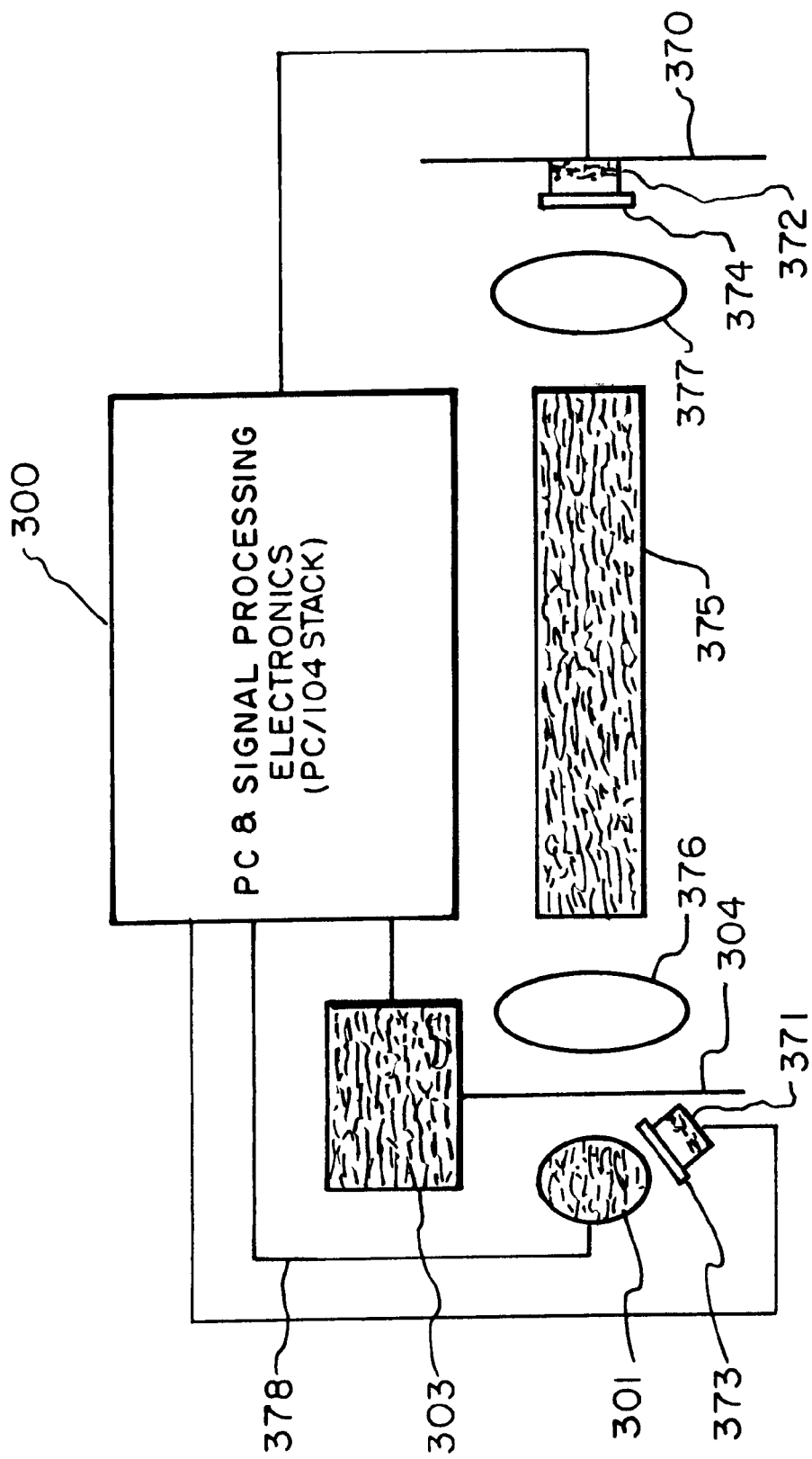
FIG. 18 is a schematic block diagram of a system for regulating the emission source to reduce high and low frequency fluctuation that can cause instrument noise and drift.

A schematic block diagram of signal processing and control of emitter or source 301 is illustrated in FIG. 18. A signal received by a pre-amplifier board 370 from detector 372 through narrow band pass optical filter (NBOF) 374 is fed to signal processing board 300 mounted on a PC/104 stack. The signal processing approach is composed of 900 Hz synchronous rectification (demodulation) followed by analog to digital conversion using an A/D converter (AD7714) programmable resolution (16–24 bits), gain (1× to 128×), and speed (5–60 Hz) analog to digital conversion (ADC).

In addition the system shown in FIG. 18 includes a feedback loop for control of a IR source. Other efforts involved the use of a photodiode and a feedback loop to regular the IR source such as that shown in U.S. Pat. No. 5,457,320 of R. D. Eckles et al. However, this system merely controls the visible emission from the source and not the IR. The present system employs a NBOF 373 adjacent IR source 301 and a thermopile 371 to measure photon density of radiation from IR source 301. Thermopile 371 gives a direct reading of radiation using measurement-of the gas in measurement cell 375 rather than an indirect measurement that would be obtained by a photodiode. The advantage of this configuration is that narrow band optical filter 373 can be used to isolate the same spectral window as the one used in the measurement of the gas by the instrument (e.g., 2,100 cm$^{-1}$ for carbon monoxide). IR source 301 is then controlled by feedback from thermopile 371 to signal processing electronics 300 and feedback loop 378. Thus regulation of IR source 301 using analyzer signal processing electronics 300 and feedback loop 378 is more efficient than previous methods thereby allowing ultra-high precision work to be carried out with the instrument.

The system also has another unique feature of employing a miniature lens directly mounted to the detector assembly to optically compensate for vibration effects, insuring that the beam is focused onto the detector even when the angle of incidence onto the lens changes. Thus, narrow band pass optical filter 374 can be provided with a miniature lens directly attached to detector 372.

With the modular circuit design and PC/104 architecture standard the system can accommodate a variety of detector types that allow detecting anything from short wavelength ultraviolet (UV) to long wavelength infrared (IR). Thus with the modular construction and interchangeable detector types, the system is usable from vacuum UV all the way out to the far IR. Also with the PC/104 configuration and architecture, one signal processing board for detection of one group can be quickly and easily removed and a different signal processing board plugged in that goes to a different range of detectors to detect a different group. This modular interface in which the detector may be changed with the software remaining the same allows the signal processing board to be taken out and replaced by another to permit access to a completely new range of detectors.

Basically there will be only two boards. One is a detector board or pre-amplification board 370 which is a small board on in which detector 372 itself is usually mounted. This board basically takes the signal from detector 372 and filters it (i.e., analog filtering) and then gives it one or more stages of amplification. Pre-amplifier board 370 also controls detector temperature and would have a temperature controller if detector temperature control is necessary. Pre-amplifier board 370 feeds signal from detector 372 to a signal processing board 300 which is on a PC/104 architecture stack. Detector pre-amplifier board 370 is not on the PC/104 stack.

There may be a detector pre-amplifier board 370 for each type of detector since each type of detector is different. A silicon detector could be used in the UV, a lead selenide detector in the mid infra-red, a mercury-cadmium-telluride detector in the far IR, etc. There are many possible detectors and for each detector, there is a preamplifier board but it may be possible to use the same preamplifier board for some different detectors. All pre-amplifier boards 370 are designed. to interface with PC/104 stack or signal processing board 300 so the head of the electronics is the same. Pre-amplifier board 370 feeds a detected signal to the input to signal processing board 300. Once it gets to the signal processing board, the same signal processing board can be used for a whole range of detectors.

Signal processing has a frequency associated with it which is the frequency at which light is modulated at detector 372. That is the function of the detector response time. Some detectors are fast and other detectors are slow and the system would have to accommodate for that. However, there need only be two signal processing boards for the system. That is, there is only two designs for signal processing; one is for low frequency work and the other is for high frequency. Therefore, the signal can go from DC (direct current) a constant signal without any chopping all the way to 100 Hz with one board and from 100 Hz to 100 KHz on a second board. The signal processing boards permit the use of the same software with either one of them. With the modular construction disclosed and described the system can have any detector a user wishes.

The advantage of this is that. the system now can measure multiple gases. Most systems sold are designed to analyze only one gas. While a system capable of measuring multiple gases may be more expensive when applied to measuring only a single gas, it is generally less expensive than multiple single gas analyzers for those applications where multiple gas measurements are needed. Another advantage of the system is that it has expansion capabilities. It is easy to take the basic instrument or system and add another measurement or replace a measurement as the laws change and regulations tighten and the measurement level must be reduced or possibly increased but nevertheless it changes. This modular system with interchangeable detectors enhances that capability.

FIGS. 7 and 8 illustrate that many of the advantages of this invention can be attained with a different means to mount the cells ("filters"), and without using a rotatable deflector. In FIG. 7, a wheel 350 is shown bi-directionally rotatable around an axis 351 which is parallel to and offset from path 327. Wheel 350 has a plurality of ports 328, 329, 330 and 331, each adapted to hold a respective cell or filter. In fact wheel 350 could contain six, eight, or more cells. A detector 355 receives energy passed by the cells. It is evident that the position of the source and the detector can be reversed in this embodiment.

In the embodiments already described, the gases in the gas stream (or open-path) are traversed by the beam or are used as a source. It is equally within the scope of this invention to divert gas through a sampling chamber, and to use the gases in the sampling chamber the same as the gases in the stack. FIG. 10 shows a sampling chamber 340 with an inlet 341 and an outlet 342. Stack gases are diverted through the chamber, which is equipped with windows 343, 344. A reflector 345 is at one side, and the transceiver 346 (the analyzer and source) is at the other. All features of any of the embodiments are useful with the sampling chamber, or with the stack.

In the previous embodiments, gas cells have been disclosed as the band pass filters. Instead optical filters can be used in place of one or more of them and this is particularly true when the subject gas or gases is or are of the type whose absorption spectrum is a broad band instead of a group of spaced-apart lines. Examples of suitable optical filters are those which are built by Optical Coating Laboratory, Inc., of Santa Rosa, Calif. Their precise construction is maintained as proprietary information by this company, but one can order filters with suitable properties. These filters are built up on an optical substrate with multiple dielectric layers to achieve the desired narrow band pass feature. With these, a pair of filters will generally be used, with the notch of one close to but not overlapping the notch of the other.

In this specification, the term "filter" is used generically both for optical filters and for gas cells.

FIG. 11 shows a wheel 400 with the same objectives as the device of FIG. 8. It has ears 401, 402 and 403, with ports 404a, 404b, 405a, 405b, 406a and 406b passing through them. There may be more or fewer than three of them. These represent pairs of associated filters, and the wheel can be stepped between pairs, and between members of any pair.

FIG. 12 shows an optical filter 407 in port 404a.

FIG. 13 shows optical filter 407 backed up by a fully reflecting mirror 408 should reflection be desired.

FIG. 14 shows a gas containing cell in port 404a.

FIG. 15 shows a transceiver 415 according to any of the embodiments of this invention. Instead of receiving a direct reflection as before, three fully reflecting mirrors 416, 417, 418 (beam reflecting means) are provided to establish a perimeter comprising beam segments 419, 420, 421, 422. Beam 422 is received by the transceiver, and analyzed as before. Only the beam reflecting means is modified. Of course means is provided to direct beam 422 appropriately within transceiver 415.

The arrangement of FIGS. 15 and 16 provides surveillance for an area 423. It will give evidence that within the total path there is a given concentration of a substance, or give warning that it is there at all. This is useful in monitoring regions that are likely to emit toxic materials.

Should a more localized indication be desired, then a barrier rather than a perimeter will be established. FIG. 17 shows a transceiver 425 and reflector means 426 according to any embodiment of this invention. The directed beam 427 and reflected beam 428 are both indicated by the same line in FIG. 17. In the event that emitted energy is being analyzed, then the system of FIG. 6 would be provided, and focused along the axis indicated by reflected beam 428 in FIG. 17.

While infra-red radiation has been shown as the preferred energy beam, for some applications visible or ultra-violet wavelengths may be even more suitable. This invention is adaptable to any such type of energy. Of course the filters will be appropriately selected.

While the monitoring of combustion processes by analysis of their stack gases is a very substantial proportion of the present applications for this invention, the detection, monitoring and measurement of other compounds is becoming increasingly important. Toxic compounds such as PCB, chlorinated dibenzodioxins, other hydrocarbons which are toxic, phosphorus compounds, and pesticides are examples. In combustion control and in air pollution monitoring, carbon monoxide, nitrogen oxides, and sulfur dioxide remain the compounds of primary importance.

In this specification, the term "analyzer" is used for that portion of the system in which the beam and the filters are brought together. That part of the system in which the calibration beam is formed, or the beam passed through the sample, is sometimes called "beam forwarding means."

The operation of the system as to absorption or emission, utilizing the principles and particles of filter correlation (whether gas is used for the filter means, or an equivalent optical filter is used instead) will be recognized by persons skilled in the art. This instrument and the applications it enables, is rugged and involves few moving parts. Importantly, it is forgiving for changes in alignment, and in some embodiments can be constructed so as to require only the movement of beam segments, rather than of filters, as a consequence of the simple stepping movement of a mirror-bearing deflector.

Spectral energy, i.e., wave type energy subject to absorption or emission interaction can be used, over the full range of spectral wavelengths, including ultraviolet, visible, and infra-red. Of course, an appropriate emitter and responsive deflector must be provided. For most gas measurements, the infra-red region is very suitable, and detectors responsive to wavelengths in this region are well developed. However, the invention is not to be limited to usage in the infra-red region, because absorption and emission phenomena in other bands or regions are also useful.

Systems according to this invention are elegantly simple and inherently rugged. The image-deflecting and forming elements are simple lenses and reflectors. Sharp images are not necessary, because it is only necessary that the beam be related to selected filters from time to time, and then arrive at the active surface of the detector. In some embodiments this instrument can be switched from calibration to measurement modes merely by shifting a shutter, and operates within its measurement mode merely by appropriate rotation of a mount which carries reflecting surfaces. In another.embodiment the change of modes is made merely by shifting a retroreflector.

This invention is not to be limited by the embodiments shown in the drawings and described in the description, which are given by way of example and not of limitation, but only in accordance with the scope of the appended claims.

What is claimed is:

1. An instrument for detecting the presence of or for measuring the concentration of a gas in a large stream of other gases comprising;

a spectral energy beam emitter for emitting a beam of spectral energy across said large stream of gasses;

an analyzer for receiving and analyzing said beam of spectral energy that has passed through and been converted from at least some part of said large stream of gases;

a plurality of narrow band pass filters through which said beam of spectral energy is passed;

an in-situ calibration audit cell for calibration across said large stream of gases, said audit cell comprising a cell having a fixed length filled with a high concentration reference gas proportioned to the gas concentration;

whereby an in-situ calibration across said large stream of gases can be performed without removal of said analyzer.

2. The instrument according to claim 1 in which the length of the cell is filled with a gas that is proportional to an isotope of the preference cylinder gas.

3. The instrument according to claim 2 including means for calculating system zero by an incremental additions method.

4. The instrument according to claim 3 in which said means for calculating system zero and span comprises means for evaluating by an iterative regression comprised of varying the reference cylinder gas and recording readings for each variation of calibration reference gas.

5. The instrument according to claim 3 including means for varying the reference cylinder gas in said audit cell.

6. The instrument according to claim 1 including means in which said beam of spectral energy is a source of IR spectral energy.

7. The instrument according to claim 6, including means for dynamically controlling the emission of said IR source comprises means for measuring the photon density of radiation from said source; connecting the output of said photon density measuring means to a feed back loop to compensate for instrument noise and drift.

8. The instrument according to claim 7 in which said means for controlling emissions of said IR source includes a narrow band pass optical filter.

9. The instrument according to claim 8 in which said means for measuring the photon density from said source comprises a thermopile.

* * * * *